United States Patent [19]
Doherty et al.

[11] Patent Number: 5,997,545
[45] Date of Patent: Dec. 7, 1999

[54] KNEE INCISION TENSILE GAUGE

[75] Inventors: Thomas Vincent Doherty, Dorchester; Erik Scott Larson, Norwood; Richard D. Scott, Dedham, all of Mass.

[73] Assignee: Johnson & Johnson Professional, Inc., Raynham, Mass.

[21] Appl. No.: 09/187,904

[22] Filed: Nov. 6, 1998

[51] Int. Cl.⁶ .................................................. A61B 17/58
[52] U.S. Cl. .......................................... 606/102; 606/206
[58] Field of Search .......................... 606/102, 205–209, 606/120, 122, 151; 600/215, 220, 201, 202, 210, 219, 184; D7/686; 73/81; 294/110.1

[56] References Cited

U.S. PATENT DOCUMENTS

| | | | |
|---|---|---|---|
| 2,715,403 | 8/1955 | Tucker | 606/205 |
| 3,696,662 | 10/1972 | Foltz et al. | 73/81 |
| 3,785,381 | 1/1974 | Lower et al. | 606/122 |
| 4,413,635 | 11/1983 | Myer | 600/595 |
| 5,047,046 | 9/1991 | Bodoia | 606/205 |
| 5,294,162 | 3/1994 | Grimes | 294/110.1 |
| 5,735,857 | 4/1998 | Lane | 606/99 |

*Primary Examiner*—Michael Buiz
*Assistant Examiner*—Jonathan D. Goldberg
*Attorney, Agent, or Firm*—Nutter, McClennen & Fish, LLP

[57] ABSTRACT

A tool for measuring tissue tension during joint surgery has a tissue gripping end and a measurement assembly. The tool is preferably configured as a pair of tongs, with a mechanism that fixes the tongs to grip tissue with its tissue gripping end while the measurement assembly measures the tension in, or spreading force applied on the tissue gripped therein. In use, the joint is moved through a range of motion while the tool is attached, and the measurement assembly displays changes in tissue tension due to movement of the joint. A prototype tool implemented as a pair of tongs has tissue-gripping pincer points that are held closed by a ratchet bar assembly. The ratchet bar assembly is a telescoping cross bar which moves against the restraining force of an extension spring to register the spreading force exerted on the pincer arms by the tissue under tension. An annular stop member about each pincer point limits tissue penetration, and provides a defined surface against which the tissue acts allowing precise calibration of the device.

9 Claims, 4 Drawing Sheets

KNEE INCISION TENSILE GAUGE

CROSS REFERENCE TO RELATED APPLICATION

Not Applicable.

STATEMENT REGARDING FEDERALLY SPONSORED RESEARCH

Not Applicable.

FIELD OF INVENTION

The present invention relates to tools and instruments for knee surgery, and particularly for knee surgery related to the installation of prosthetic knee joints.

BACKGROUND OF THE INVENTION

Knee arthroplasty, and particularly the surgical undertaking of a total knee replacement is generally a complex procedure, which substitutes prosthetic structures for the normal or natural geometry of the articulation surfaces, and frequently must accommodate prior damage to one or more ligaments, bones or tissue structures of the joint, and biological changes or distortions which have evolved therefrom. In general, it is necessary to perform soft tissue balancing and numerous specially aligned cuts at the bone ends in order to install the prosthetic components with correct spacing, alignment and tensioning to prevent improper kinematics from arising as the joint rotates in use, and to avoid the occurrence of accelerated wear patterns or possible joint dislocation. Typically, this requires a number of measurement steps and cutting or fitting steps, often with additional small adjustment cuts to achieve final bone preparation for mounting the metallic and other components of the prosthetic joint. Preliminary soft tissue balancing may be accomplished when the gaps at the bone ends are formed in extension and flexion, for receiving the prosthetic endings. Thereafter, various additional fitting steps may be required to achieve proper patella tracking, and additional soft tissue balancing or adjustment may be required for the patellar tendon, i.e. the quadriceps tendon and the patellar ligament, which together surround and extend from the patella at its upper and lower ends respectively.

Soft tissue tensioning, e.g. surgical relief of the medial and lateral and collateral ligaments and of the patellar tendon, is generally performed by feel, with the surgeon sensing the tension exerted by the relevant soft tissue structure as the major bones are moved through various positions relative to each other. Such tensioning is necessary because tendons and ligaments are relatively inextensible, and the provision of a new joint geometry defined by the prosthetic components may result in the build-up of extreme tensile forces or excessive looseness in one or more positions, as well as lateral forces due to the displacement of one or more surfaces or axes of the prosthesis from those of the natural joint or previous prosthesis it replaces.

It would therefore be desirable to provide a tool to more effectively determine the tensile forces of the relevant tissue, and to conveniently assess tension at various stages of the procedure, both for identifying initial values, and for subsequently correcting changes in the tensile loading occasioned by the new joint geometry of the prosthesis.

SUMMARY OF THE INVENTION

These and other desirable ends are attained by a tool in accordance with the present invention and a method of using a tool wherein opposing pincers are urged into contact with tissue and a force measuring mechanism determines the force exerted by the tissue as the knee is brought through a range of motion. A ratchet mechanism across the handle sets the pincers in a neutral tissue-gripping position, and a force measuring mechanism, which may include a sliding rod and spring assembly, reads off the reactive force applied by the tissue on the pincers. In a preferred embodiment, the pincers are implemented as a tong assembly having a scissor-like pair of crossing hand grips with curved arms that come to respective pointed terminal ends, similar in overall shape to a pair of ice tongs. An annular or disc-like stop member spaced near each point defines a depth of penetration and a presents a defined surface area against which the tissue exerts its reactive force, while the spring measuring mechanism, attached between the two arms at the handle end, measures that force. In a prototype embodiment, the measurement assembly includes inner and outer telescoping cross bars attached to the respective handles, with a spring fitted about the inner bar to permit a limited range of relative motion, and the position of the inner bar is indicated by a cross pin which moves next to graduation marks on the outer member. The outer member is attached to one of the handles by a ratchet release mechanism, allowing the initial overall length of the cross bar assembly, and correspondingly the pincer spacing, to be conveniently and automatically set as the pincers are closed on a tendon, sliding the bar in one direction to the point of initial tissue resistance.

In a representative method of use, the pincers are brought into firm gripping contact about the capsule and tendon while the knee is in extension, and the handles are squeezed together such that the nominal spring tension is zero. The leg is then rotated through a range of movement, while the applied resisting force, which indicates the increasing tissue tension, hence the degree of resistance to tissue separation as the joint rotates, is observed on the pin graduation scale of the cross member. The surgeon may then free up the ends of the tendon or ligaments to reduce excess strain, or may otherwise adjust the prosthesis fitting to achieve proper patella tracking, before closing up the surgical incision. The tool may also be used to determine and record one or more baseline tissue tension measurements, allowing the surgeon at the end of the operation to match the tension to the recorded level which was naturally accommodated by the tissue prior to replacement.

BRIEF DESCRIPTION OF THE DRAWINGS

The invention will be better understood from the following description of illustrative embodiments, taken together with the drawings in which.

DETAILED DESCRIPTION OF ILLUSTRATIVE EMBODIMENT

Figure 1:
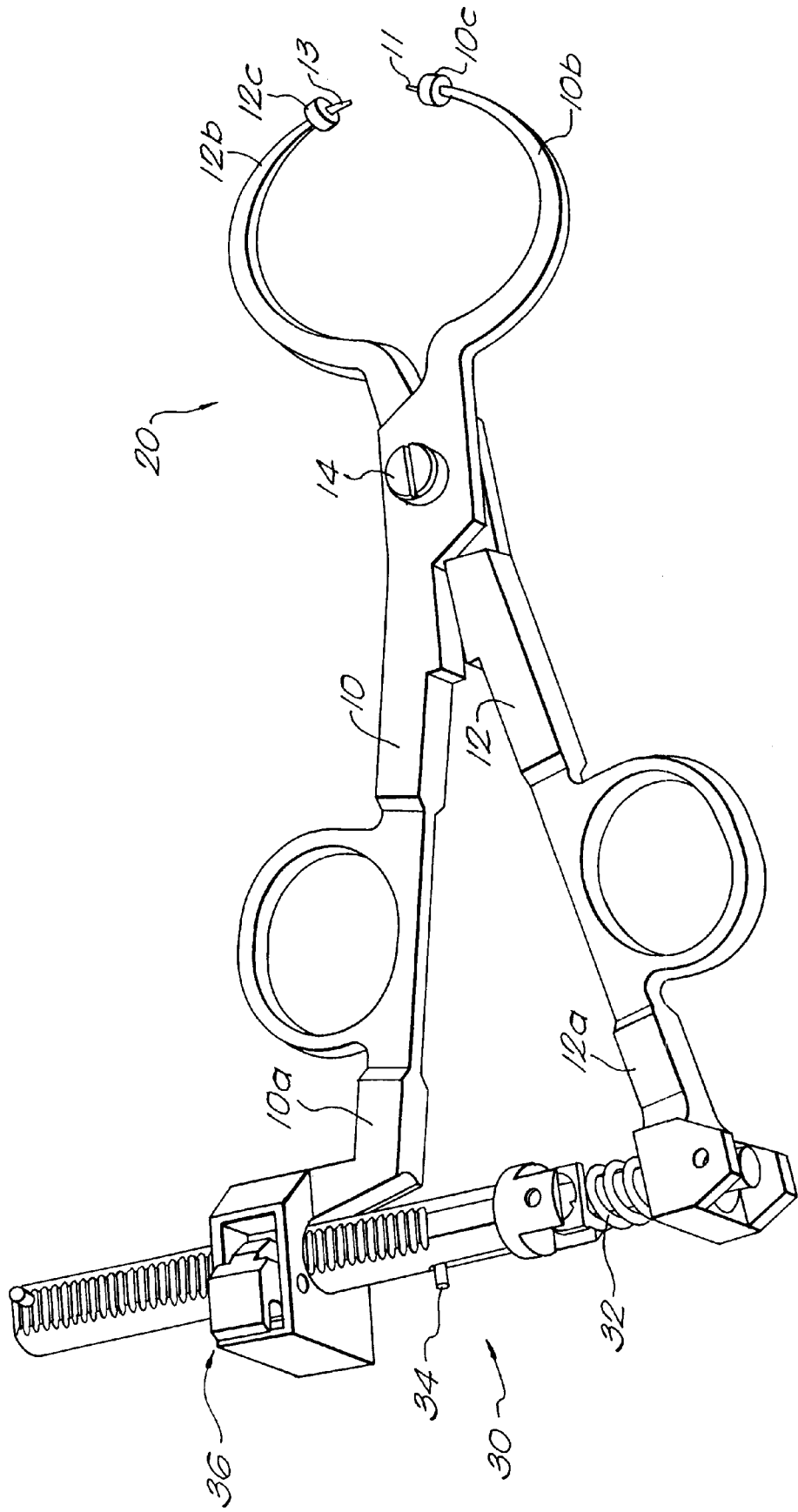
FIG. 1 illustrates one embodiment of a tool according to the present invention.

FIG. 1 shows a prototype embodiment 20 of a knee incision tensile gauge in accordance with the present invention. The tensile gauge 20 is configured as tongs having a pair of arms 10, 12, each arm having at one end a pincer arm 10b or 12b with a respective pincer point 11 or 13 respectively, and having at its other end a shank 10a, 12a with a force measurement assembly 30 connecting the shanks 10a, 12a. The pincer arms 10b, 12b are each curved to allow a high degree of relief so that their pointed terminal ends may reach the relevant tissue structures, e.g., the tendons and ligaments of the joint. Each arm preferably includes a stop member 10c,12c respectively, for limiting the depth of penetration of the pincer points 11,13 and presenting a defined surface against which the tissue presses as it is tensioned. As shown generally in FIG. 1, a force measurement assembly 30 connects between the two arms and includes a spring force mechanism 32, a pointer mechanism 34 which indicates the spring displacement or relative spacing of the two arms from a set position, and a ratchet mechanism 36 for setting the initial handle position or tissue gripping gap. The pointer mechanism is spring mounted so that its position depends on the force between arms 10, 12. The arms 10, 12 are formed with a scissors-like handle grip (not numbered) allowing the tool to be conveniently held and manipulated by placing the fingers through the handle openings.

Figure 2:
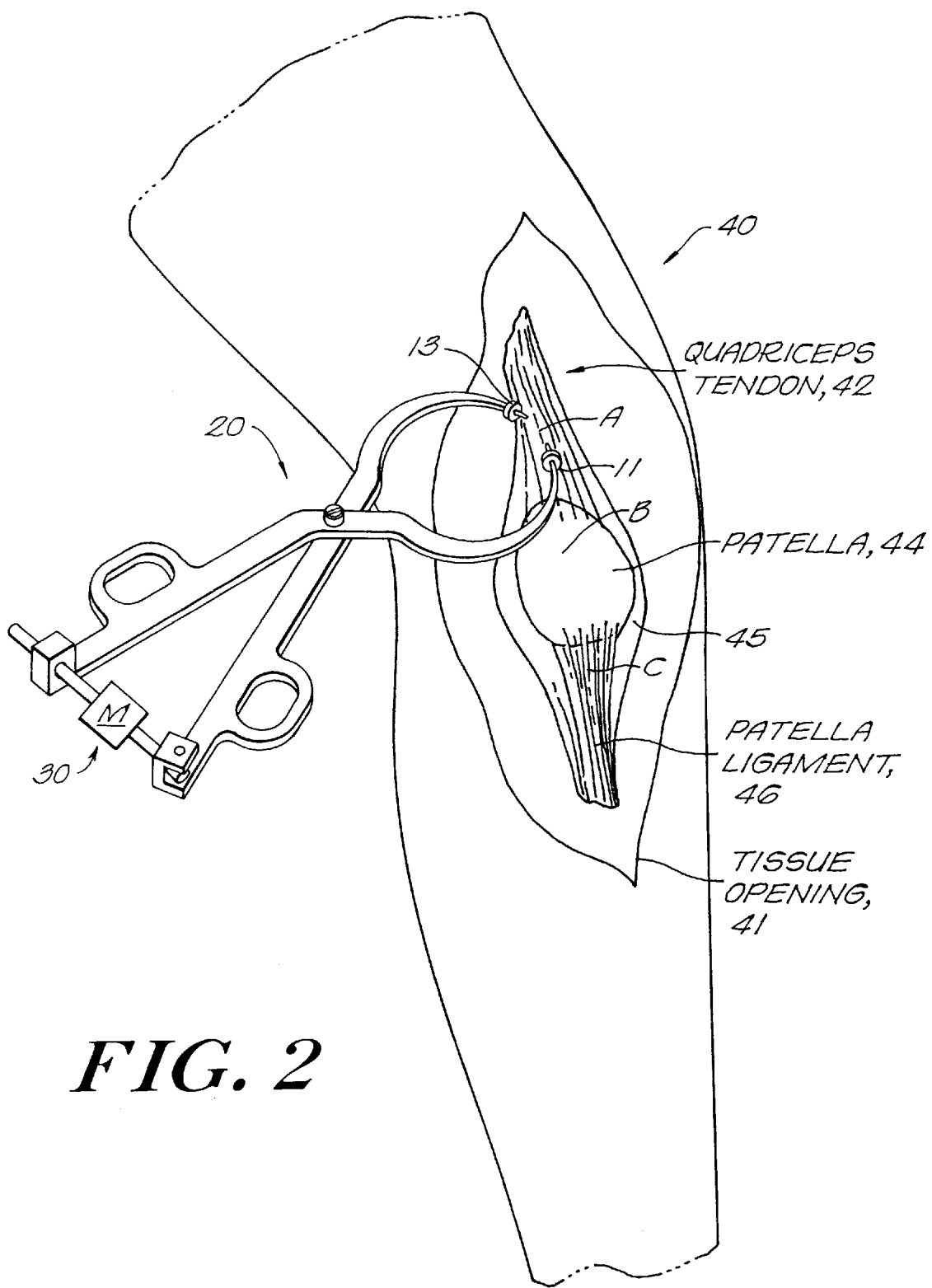
FIG. 2 is a perspective view showing the tool in use.

FIG. 2 shows the tool 20 in use. As shown, the prongs 11, 13 and measurement gauge 30 are used in the vertical incision or tissue opening 21 during knee surgery. In particular, the gauge may be clamped to the quadriceps tendon 42 such that one prong 11 sticks into the tendon while the opposing prong 13 engages the capsule from the opposite side. When so engaged, the measurement assembly 30 is initially set to a resting position, and thereafter indicates the degree of resisting force from the tissue pushing against the two prongs as the tissue is stretched by separating movement of the joint. The measurement assembly 30 illustrated by a unit M may have an electrical display or a mechanical pointer.

As noted above, the assembly is initially set by the ratchet adjustment member 36 (FIG. 1), so that the tension reading is zero. This is accomplished by manually closing the tongs on the relevant tissue, allowing the ratchet bar to slide to the clamped position. The knee is then moved between flexion and extension positions while the gauge 30 is observed. As the knee is moved, separating force applied by the joint to the connecting tissue results in a pushing-apart of the pincers, so that the spring extends and the pin and graduation assembly provides a measure of the magnitude of the tissue tension.

Other relevant tissue structures shown in FIG. 2 are the patellar tendon 46, the patella 44 and the prepatellar bursa (indicated generally by 45) which carries the patella. In general, the gauge may be clamped at position A, on the quadriceps tendon, position B on the prepatellar bursa or bundle, or position C on the patella ligament 46. Position B is preferred for generally assessing the degree of tension over the patella as the knee is flexed. The gauge 20 offers the prospect of forming quantitative measurements of the tissue tension under normal and post-surgical conditions. A normal range of tissue tension has been found in a preliminary series of measurements to be in the range of somewhat under 10 to about 20 pounds. Applicant believes it to be desirable that the prosthesis be fitted such that the tensile forces acting on the tendons and ligaments are not greatly increased from the initial values thereof.

Figure 3:
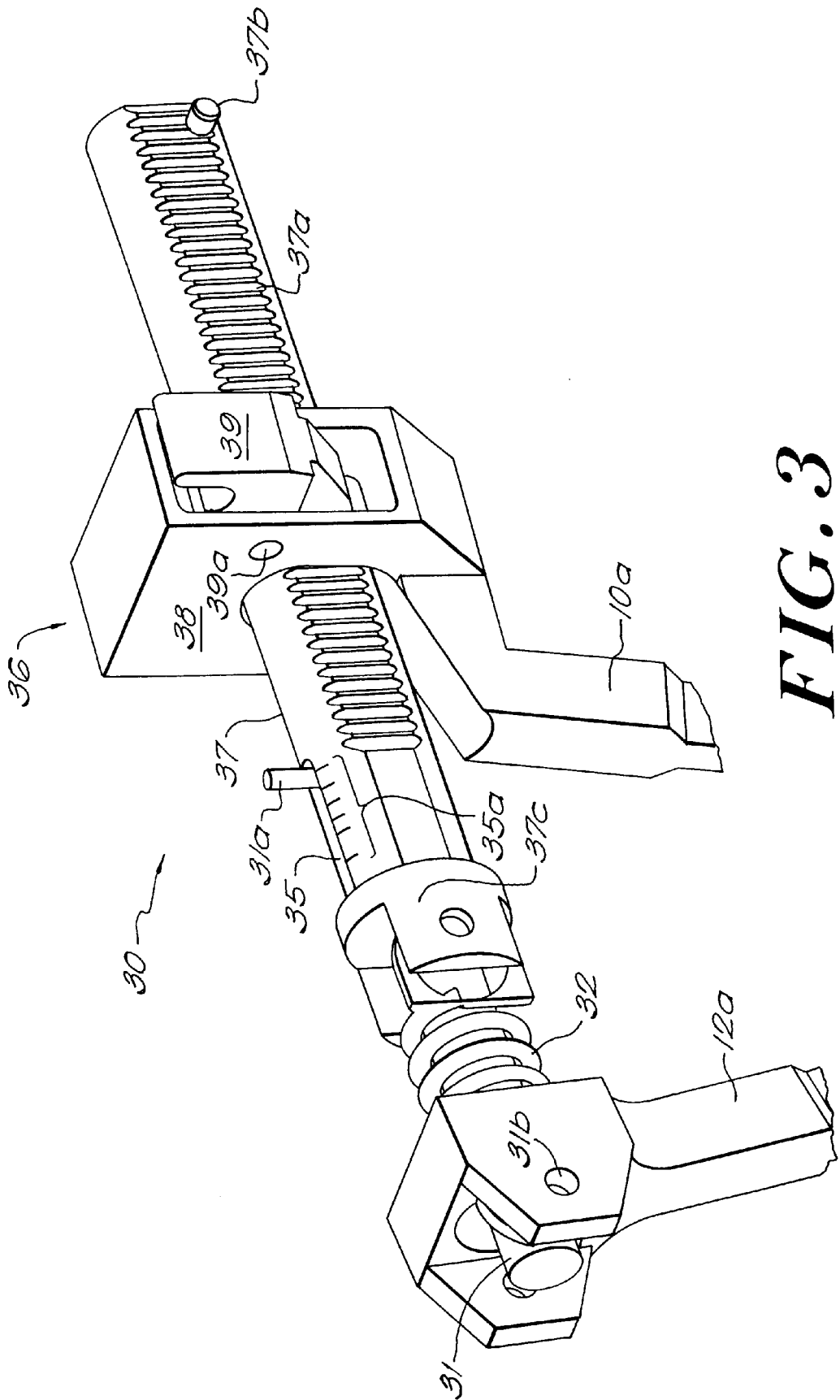
FIG. 3 shows the force measurement assembly of the prototype embodiment of FIG. 1.

As noted above, the resisting force of the tissue, indicative of the separating strain caused by motion of the articular components of the joint, is measured by the force exerted on the pincers via fulcrum 14 and arms 10, 12, on the measurement assembly 30. FIG. 3 shows the prototype assembly 30 in greater detail. As shown, the measurement assembly 30 extends between one end 12a of the arm 12 and the corresponding end 10a of the arm 10, and has a first component 31 carried by the end 12a and a second component, namely the ratcheting assembly 36, engaged by the end 10a. The ratcheting assembly 36 is comprised of an elongated cylindrical or tube-like cross-member 37 having a line of ratchet notches 37a formed along its length, and a guiding and gripping structure 38 in which the cross-member 37 slides. A pawl grips the ratchet notches, and a spring-loaded pawl release button 39 pivots on a pin 39a in the housing 38 to engage the ratchet grooves 37a or release the groove and allow free sliding movement of the cross-member 37. Attached to one end of member 37 is a stop pin 37b which defines the maximum length of travel of the cross-member, while the other end has a cap 37c affixed thereto which engages one end of the spring 32.

The end of the rod 31 is pinned to the end 12a by a cross-pin 31b, and the rod itself passes centrally through the spring 32 and slides telescopically within the hollow cross-member, ratchet rod 37. The rod 31 also carries an indicator pin 31a, which extends out through a slot 35 in the cross-member 37, so that the position of the pin 31a provides an indication of the degree of extension of rod 31 within the surrounding cross-member 37. Thus, the position of the rod within the assembly, as indicated by pin 31a and graduations 35a next to the slot 35, reports the spreading force applied by tissue against the pincers and arms to extend the spring 32. The spring 32 is chosen so that its length in the resting state positions the pin 31a at one end of the line of graduations, whereas when the prongs 11, 13 are urged apart, the spring length will extend over a range of about 2 centimeters under a tensile force of about 0 to 20 pounds. As shown generally in FIG. 1, the ratio of actual tissue tension or force at the prongs 11,13 may be somewhat less, or may be several times more than that experienced by the spring, owing to leverage of the pincer arms about the relative position of pivot 14 in the tongs assembly. However, the force is further dependent on the areas of the annular stops 10c, 12c. All of the foregoing scale factors or values may be viewed as arbitrary in the prototype embodiment, and these may be adjusted or refined in further embodiments so that the measurement assembly has a greater range, or a greater sensitivity, employing springs of different length or different spring constant, or stops of different proportion, in which the measurements are adjusted to allow the prongs to more readily reach or grip the target tissue, and the scale is set to accurately refect the prevailing range of tension.

In the foregoing embodiment, the ratchet assembly 36 allows the prongs to be brought together to grip a tendon, ligament or other tissue structure of arbitrary size, typically opening to a gap of approximately one-half inch to allow placement around the tissue, and closing so that the points 11,13 penetrate the tissue, are nearly touching and clamp the tissue between the opposed stops 10c,12c. The ratcheting cross-member 37 and pawl/release 39 allow the tensile gauge to be zeroed when gripping the tissue, after which motion of the pin 31a indicates changes in cross-extension from the initial state, which is set with the knee in extension and the tendon relaxed.

Figure 4:
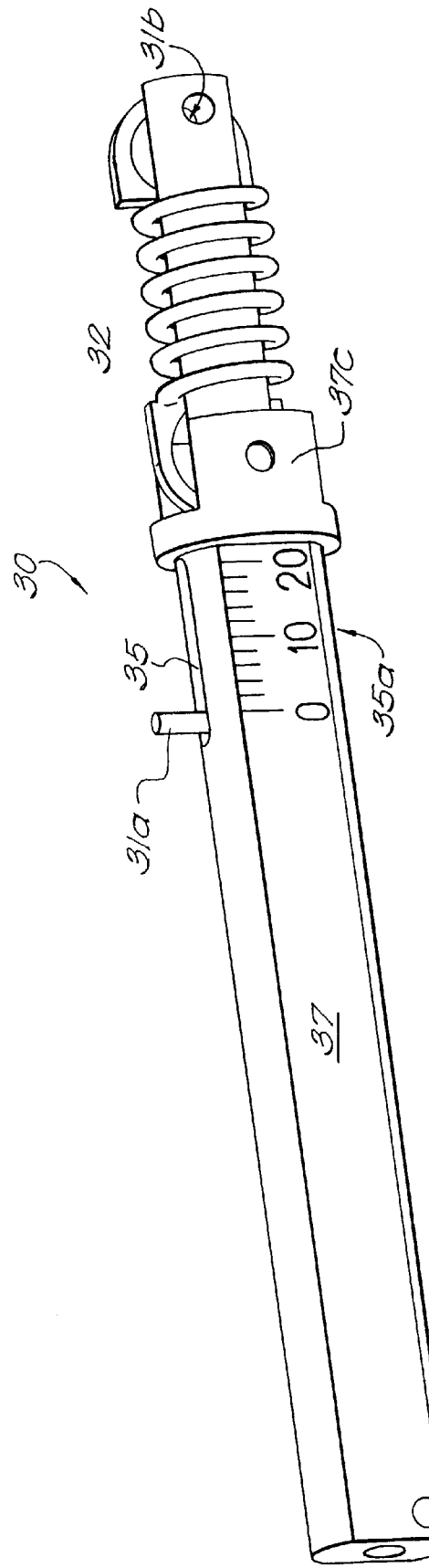
FIG. 4 shows details of the measurement assembly.

FIG. 4 shows further details of the tension measuring assembly 30. As shown, the marker pin 31a slides in the slot 35 adjacent a set of graduations 35a which are ruled on the outside of the cross-member 37. The spring 32 is an extension spring, the length of which varies has the pin 31b of handle 12 is urged away from the cap 37c of the cross-member 37. The ratchet notches 37a are directionally cut and configured such that the ends 12a,10a move freely in one direction, so they may be urged together to grip the tissue and thereafter the ratchet holds the ends 12a, 10a from separating so that the only motion possible is by sliding of the rod 31 against the tension of spring 32, thereby indicating the force being exerted by the tissue gripped in the prongs.

In use, the surgeon grips tissue such as the quadriceps tendon (FIG. 2, region "A"), or the patella capsule (region "B") or ligament (region "C"), and then reads the changes in tension as the leg is brought through a range of motion. He may then adjust the tension or free up tissue at its region of attachment to reduce tightness, or to assure that the tissue remains balanced through the expected range of motion of the leg and prosthesis. Advantageously, the tensile gauge may generally remain in position, gripping the tissue and displaying the tissue tension during the surgical adjustment.

It will be understood that while the tensile gauge of the present invention has been described with reference to a prototype embodiment configured for use in knee arthroplasty, it may be used for gauging tissue tension in other surgical contexts. Furthermore, the particular sub-assemblies, such as the spring force gauge and the gripping prongs, may in different embodiments, take other forms, and be implemented with substitution of different substructures such as strain gauges, calipers, cam clamps and the like.

Thus, a basic embodiment of a tool in accordance with the present invention and its method of use during arthroplasty being disclosed and described, further variations in modifications will occur to those skilled in the art, and all such variations and modifications are considered to lie within the spirit and scope of the invention described herein, as defined by the claims appended hereto and their equivalents.

What is claimed is:

1. A tool for measuring tissue tension during joint surgery, such tool comprising
    a tissue gripping assembly including opposed jaw elements configured to grip tissue therebetween a mechanism for fixing said opposed jaw elements in a clamped state, and
    a measurement assembly operative to measure spreading force applied to said opposed elements by tissue gripped therein as the joint moves through a range of motion and tension in the tissue changes.

2. A tool according to claim 1, configured as a pair of tongs, and wherein said gripping assembly comprises pincer points of said tongs.

3. A tool according to claim 1, wherein the tissue gripping assembly comprises a pair of opposed tissue penetrating pincer points and a stop member about each point, wherein the points fix position of the gripping assembly in tissue such that tensile strain in the tissue exerts reactive force against the stop members.

4. A tool according to claim 2, wherein the measurement assembly comprises a spring extension assembly positioned across said tongs.

5. A tool according to claim 1, wherein said measurement assembly is selected from among an extension spring, a strain gauge, and a compression spring.

6. A tool according to claim 5, wherein said measurement assembly indicates tension by a mechanical display.

7. A tool according to claim 5, wherein said measurement assembly indicates tissue tension by an electrically driven display.

8. A tool for checking tension of a tendon, ligament or the like during arthroplasty, such tool comprising
    opposed pincer points configured for engaging tissue therebetween a spring biasing said points together and extending in response to spreading force exerted on the points by tissue engaged therebetween
    means for fixing said pincer points in a clamped position, and
    an indicator operative to indicate the tension of the tissue as the spreading force varies due to joint movement.

9. A tool according to claim 8, wherein the tool further comprises caliper arms, said caliper arms having said points disposed at ends thereof and being contoured for providing relief so as to effectively position said pincer points about the patellar tendon during surgery.

* * * * *